(12) United States Patent
Warby

(10) Patent No.: US 7,926,482 B2
(45) Date of Patent: Apr. 19, 2011

(54) DISPENSING APPARATUS

(75) Inventor: Richard John Warby, Wisbech (GB)

(73) Assignee: Consort Medical PLC, Hertfordshire (GB)

( * ) Notice: Subject to any disclaimer, the term of this patent is extended or adjusted under 35 U.S.C. 154(b) by 1188 days.

(21) Appl. No.: 11/587,665

(22) PCT Filed: Apr. 27, 2005

(86) PCT No.: PCT/GB2005/001601
§ 371 (c)(1), (2), (4) Date: Oct. 26, 2006

(87) PCT Pub. No.: WO2005/105187
PCT Pub. Date: Nov. 10, 2005

(65) Prior Publication Data
US 2007/0246041 A1    Oct. 25, 2007

(30) Foreign Application Priority Data
Apr. 27, 2004  (GB) .................................. 0409351.4

(51) Int. Cl.
*A61M 11/00* (2006.01)
(52) U.S. Cl. .............................. 128/200.23; 128/200.14
(58) Field of Classification Search ............ 128/200.14, 128/203.12, 203.15, 203.19; 222/504, 402.1–402.2; 251/325, 282, 129.01–129.22; 239/338
See application file for complete search history.

(56) References Cited

U.S. PATENT DOCUMENTS

| | | | |
|---|---|---|---|
| 5,193,745 A * | 3/1993 | Holm | 239/102.2 |
| 5,294,022 A | 3/1994 | Earle | |
| 5,447,150 A * | 9/1995 | Bacon | 128/200.14 |
| 5,483,953 A | 1/1996 | Cooper et al. | |
| 5,692,492 A * | 12/1997 | Bruna et al. | 128/200.23 |
| 5,881,954 A | 3/1999 | Holm | |
| 6,425,356 B1 | 7/2002 | Pischinger et al. | |
| 6,644,517 B2 * | 11/2003 | Thiel et al. | 222/402.24 |
| 2001/0015387 A1 | 8/2001 | Fuchs | |

(Continued)

FOREIGN PATENT DOCUMENTS
DE    40 37 945 A1    9/1991

(Continued)

OTHER PUBLICATIONS

Combined Search Report and Examination Report under Sections 17 &18(3) for Application No. GB0409351.4 dated Jul. 28, 2004 (4pages).

(Continued)

*Primary Examiner* — Justine R Yu
*Assistant Examiner* — Rachel T Young
(74) *Attorney, Agent, or Firm* — Smith, Gambrell & Russell L.L.P.

(57) ABSTRACT

A pressurised metered dose inhaler (1) comprising: a reservoir (2) for containing pressurised product, a valve (9) having an inlet (11) communicating with the reservoir and an outlet (14) through which product is dispensed in use, a piece of magnetisable material (5), an armature (8) extending into proximity with the valve, and an electromagnet (7) surrounding at least a portion of the armature. Wherein the armature is coupled to, or forms part of, the valve such that controlled energisation of the electromagnet causes the armature to be either attracted to or repelled from the piece of magnetisable material one or more times to operate the valve for a controlled time period to effect dispensation of a metered dose of pressurised product from the reservoir through the valve outlet.

36 Claims, 3 Drawing Sheets

U.S. PATENT DOCUMENTS

| | | | |
|---|---|---|---|
| 2002/0100775 A1* | 8/2002 | Estelle et al. | 222/504 |
| 2003/0183224 A1* | 10/2003 | Hailey | 128/200.23 |
| 2005/0035156 A1* | 2/2005 | Hersch et al. | 222/504 |
| 2006/0261300 A1* | 11/2006 | Merabet et al. | 251/65 |

FOREIGN PATENT DOCUMENTS

| | | |
|---|---|---|
| EP | 0 111 163 | 6/1984 |
| EP | 0 232 235 | 8/1987 |
| JP | 62-249656 | 10/1987 |
| JP | A-S62-249656 | 10/1987 |
| JP | 64-44864 | 2/1989 |
| JP | Y-H01-044864 | 12/1989 |
| JP | 2002530602 | 9/2002 |
| JP | A-2002-530602 | 9/2002 |
| WO | 87/04354 | 7/1987 |
| WO | 94/25176 | 11/1994 |
| WO | 00/55072 | 9/2000 |
| WO | 01/28608 | 4/2001 |
| WO | 01/41846 | 6/2001 |
| WO | 2003071037 | 8/2003 |
| WO | 2004/041339 | 5/2004 |

OTHER PUBLICATIONS

Indian Examination Report received in Mar. 2009 (1page).

* cited by examiner

DISPENSING APPARATUS

The present invention relates to a dispensing apparatus for dispensing metered doses of pressurised products, typically for inhalation via the oral or nasal passages. In particular, the invention relates to provision of a pressurised metered dose inhaler.

Pressurised metered dose inhalers are known for delivery controlled doses of medicaments and other products. It is important to be able to accurately control the volume of each metered dose of product dispensed by the pressurised metered dose inhaler. In a typical metered dose inhaler a metering valve is provided having therein a metering chamber which defines the volume of each metered dose to be dispensed. Control of the volume of the metering chamber is critical to the accurate performance of the metered dose inhaler. This can lead to high manufacturing costs and the need for rigorous testing of components to ensure that the necessary accuracy is achieved. In addition, it is known that such metering valves can be prone to variation in the volume of the metered doses dispensed during the lifetime of the valve. This can be caused by a number of factors including distortion, degradation and swelling of the components of the valve, particularly those involved in the construction of the metering chamber. It is particularly the case that the structure and stability of the seals used in such metering valves can affect the volume of the metered dose dispensed through the lifetime of the valve.

In order to attempt to overcome at least some of these problems, it is an object of the present invention to provide a dispensing apparatus in the form of a pressurised metered dose inhaler which does not rely on an accurately volumed metering chamber to control the volume of product dispensed on each actuation of the inhaler.

The present invention provides a pressurised metered dose inhaler comprising:
- a reservoir for containing pressurised product,
- a valve having an inlet communicating with the reservoir and an outlet through which product is dispensed in use,
- a piece of magnetisable material,
- an armature extending into proximity with the valve, and
- an electromagnet surrounding at least a portion of the armature,
- wherein the armature is coupled to, or forms part of, the valve such that controlled energisation of the electromagnet causes the armature to be either attracted to or repelled from the piece of magnetisable material one or more times to operate the valve for a controlled time period to effect dispensation of a metered dose of pressurised product from the reservoir through the valve outlet.

Preferably, the piece of magnetisable material is in proximity to the valve.

Attraction of the armature to the piece of magnetisable material may open the valve to effect dispensation of a metered dose of product from the reservoir through the valve outlet. Alternatively, repulsion of the armature from the piece of magnetisable material may open the valve to effect dispensation of a metered dose of product from the reservoir through the valve outlet.

Preferably, the valve comprises a valve stem axially movable within a valve body between open and closed positions, wherein with the valve stem in the open position dispensation of product through the valve outlet is enabled, wherein the armature is coupled to, or forms part of, the valve stem. The valve stem may comprise one or more flanges and wherein the armature engages the valve stem by contact with the one or more flanges.

Preferably, the armature is resilient and, in the absence of magnetic forces, acts on the valve stem to bias the valve stem into a closed position.

The valve may comprise an internal spring bias biasing the valve stem into the closed position.

Preferably, the valve stem comprises a transfer port communicating with the valve outlet and wherein the valve comprises an outer seal sealing the transfer port from the valve inlet when the valve stem is in the closed position.

Movement of the valve stem into the open position may move the transfer port past the outer seal into communication with the valve inlet to enable product dispensation through the valve via the transfer port and valve outlet.

Preferably, the outer seal is formed from an elastomeric material.

The pressurised metered dose inhaler may further comprise a permanent magnetic circuit comprising one or more permanent magnets.

In one embodiment, the piece of magnetisable material forms a single pole piece extending from the one or more permanent magnets into close proximity with the valve.

Preferably, movement of the armature into contact with the pole piece on energisation of the electromagnet with a first polarity completes the permanent magnetic circuit.

Preferably, the attractive permanent magnetic force between the pole piece and the armature when the pole piece and armature are in contact exceeds the resilience of the armature such that when the electromagnet is de-energised the pole piece and armature remain in contact.

Preferably, energisation of the electromagnet with a second, opposed, polarity causes the pole piece to repulse the armature such that the armature breaks contact with the pole piece.

In another embodiment, the pressurised metered dose inhaler comprises two pieces of magnetisable material forming two pole pieces extending from the one or more permanent magnets into close proximity with the valve to define an air gap in which the armature extends.

Preferably, energisation of the electromagnet with a first polarity moves the armature into contact with a first of the two pole pieces to complete the permanent magnetic circuit.

Preferably, the attractive permanent magnetic force between the first pole piece and the armature when the first pole piece and armature are in contact exceeds the resilience of the armature such that when the electromagnet is de-energised the first pole piece and armature remain in contact.

Preferably, energisation of the electromagnet with a second, opposed, polarity causes the armature to be attracted to a second of the two pole pieces such that the armature breaks contact with the first pole piece.

Preferably, the controlled time period of operation of the valve is between 25 and 250 ms.

Preferably, the metered dose has a volume of between 5 and 300 microlitres. More preferably, the metered dose has a volume of between 10 and 100 microlitres.

The pressurised metered dose inhaler may further comprise a pressurised product contained in the reservoir.

The pressurised product may be maintained at a pressure of between 15 and 200 psig. Typically, the pressurised product is maintained at a pressure of approximately 60 psig at a room temperature of approximately 20 degrees Celsius.

The pressurised product typically comprises a volatile propellant. The propellant may comprise one or more of HFA134a, HFA227, with or without ethanol being present at a level of between 1 and 30%.

Optionally the pressurised product contains a pharmacologically active formulation.

The pressurised metered dose inhaler may further comprise electronic means for locking out operation of the valve for a predetermined time period after each actuation of the valve.

The pressurised metered dose inhaler may further comprise an electronic dose counter.

The present invention also provides a method of dispensing a pressurised product from a metered dose inhaler of the type comprising a valve having an inlet communicating with a reservoir in which the pressurised product is contained and an outlet, comprising the steps of:

coupling an armature of an electromagnet to, or forming an armature of an electromagnet as part of, a valve stem of the valve, moving the armature of the electromagnet by controlled energisation of the electromagnet towards or away from a piece of magnetisable material one or more times so as to move the valve stem from a non-dispensing position to a dispensing position for a controlled time period to effect dispensation of a metered dose of pressurised product through the valve outlet.

Optionally, energisation of the electromagnet moves the valve into the dispensing position.

In one embodiment, on de-energisation of the electromagnet the armature is moved away from the piece of magnetisable material by resilience of the armature so as to move the valve into the non-dispensing position.

In another embodiment, the metered dose inhaler further comprises at least one permanent magnet arranged such that on de-energisation of the electromagnet the armature remains in contact with the piece of magnetisable material until the electromagnet is re-energised with a current of opposing polarity.

Preferably, the controlled time period is between 25 and 250 ms.

Preferably, the volume of the metered dose is between 5 and 300 microlitres.

The pressurised metered dose inhaler may be used with, for example, a pulmonary, nasal, or sub-lingual delivery device. A preferred use of the pressurised metered dose inhaler is in a pharmaceutical metered dose aerosol inhaler device. The term pharmaceutical as used herein is intended to encompass any pharmaceutical, compound, composition, medicament, agent or product which can be delivered or administered to a human being or animal, for example pharmaceuticals, drugs, biological and medicinal products. Examples include anti-allergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, including combinations of two or more thereof. In particular, examples include isoproterenol [alpha-(isopropylaminomethyl) protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bircarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosphate, polygalacturonate, salicylate, stearate, subacetate, succinate, sulphate, tannate, tartrate, and triethiodide, including combinations of two or more thereof. Cationic salts may also be used, for example the alkali metals, e.g. Na and K, and ammonium salts and salts of amines known in the art to be pharmaceutically acceptable, for example glycine, ethylene diamine, choline, diethanolamine, triethanolamine, octadecylamine, diethylamine, triethylamine, 1-amino-2-propanol-amino-2-(hydroxymethyl)propane-1,3-diol, and 1-(3,4-dihydroxyphenyl)-2 isopropylaminoethanol.

The pharmaceutical will typically be one which is suitable for inhalation and may be provided in any suitable form for this purpose, for example as a solution or powder suspension in a solvent or carrier liquid, for example ethanol, or isopropyl alcohol. Typical propellants are HFA134a, HFA227 and dimethyl ether.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. As will be appreciated, the pharmaceutical may comprise of one or more active ingredients, an example of which is flutiform, and may optionally be provided together with a suitable carrier, for example a liquid carrier. One or more surfactants may be included if desired.

The seals and gaskets of the valve of the pressurised metered dose inhaler may be formed from any suitable material having acceptable performance characteristics. Preferred examples include nitrile, EPDM and other thermoplastic elastomers, butyl and neoprene.

Other rigid components of the valve, such as the valve body and valve stem may be formed, for example, from polyester, nylon, acetal or similar. Alternative materials for the rigid components of the valve include stainless steel, ceramics and glass.

Embodiments of the present invention will now be described by way of example only with reference to the accompanying drawings in which.

Figure 1:
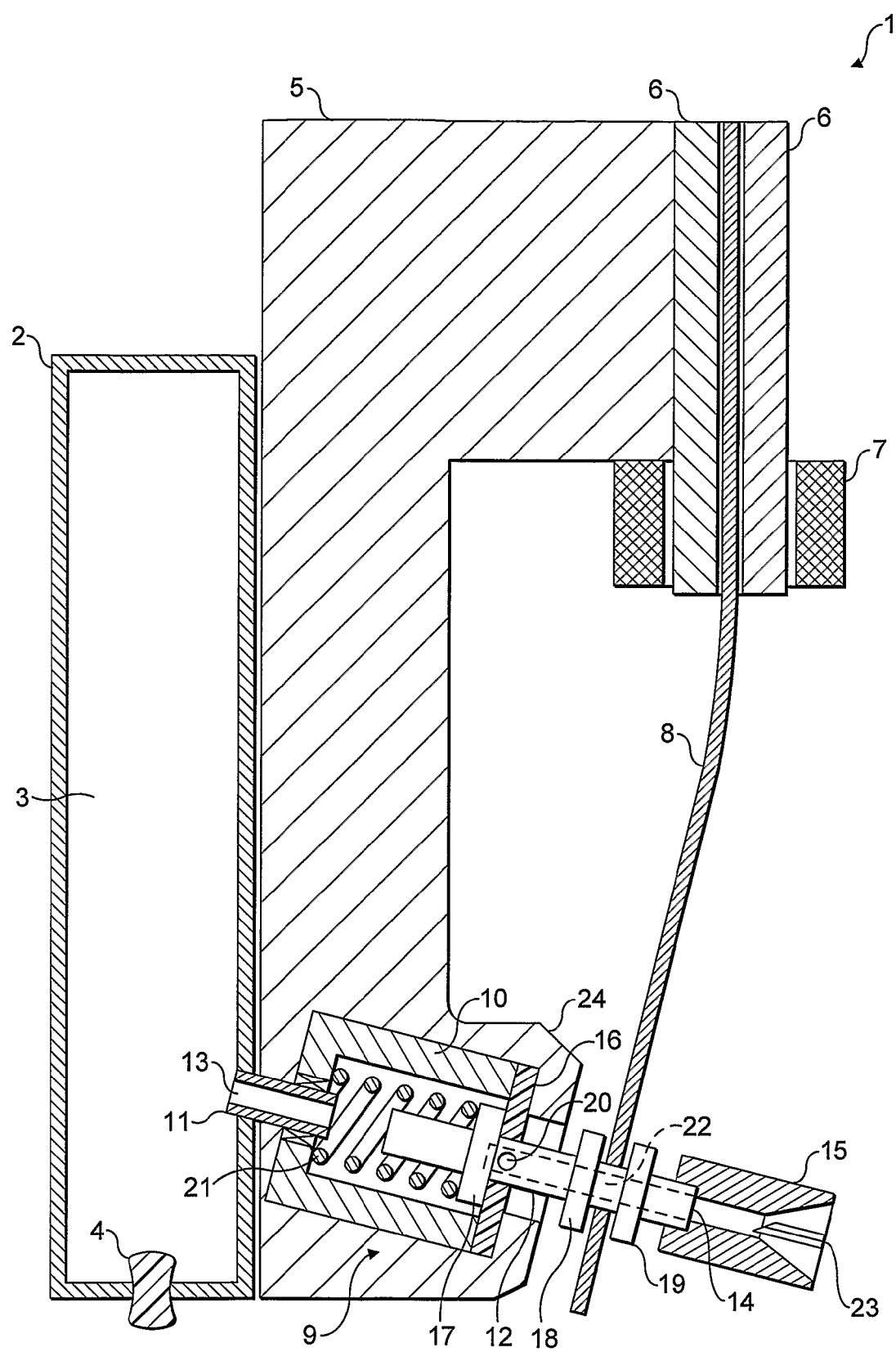
FIG. 1 is a schematic cross-sectional view through a first embodiment of dispensing apparatus in accordance with the present invention in a non-dispensing position.
Figure 2:
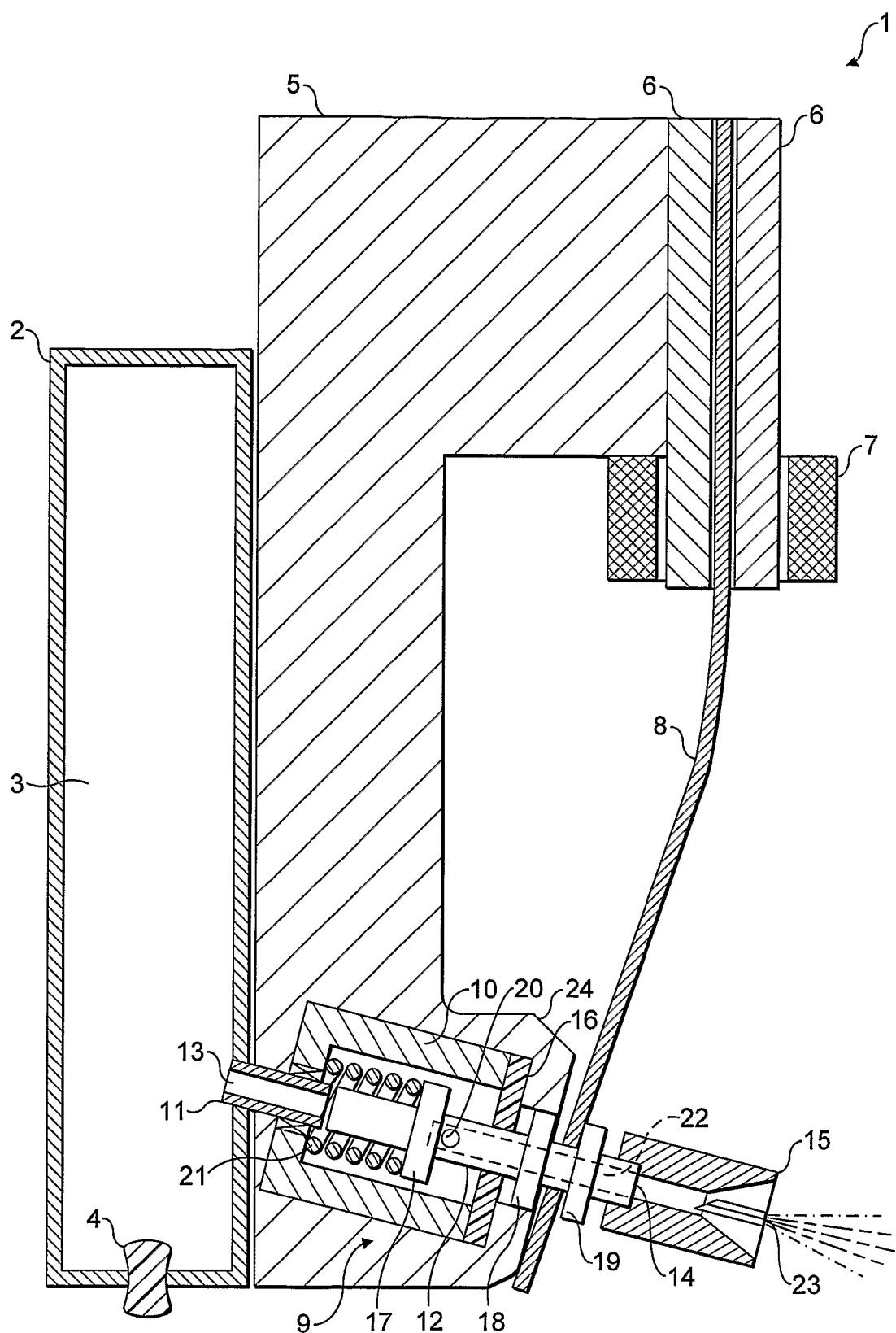
FIG. 2 is a schematic cross-sectional view of the dispensing apparatus of FIG. 1 in a dispensing position.

As shown in FIGS. 1 and 2, the dispensing apparatus 1 in the form of a pressurised metered dose inhaler comprises a reservoir 2 defining a volume 3 for holding a pressurised product in liquefied form. Typically, the product will comprise a suspension or solution of a pharmacologically active formulation together with a volatile propellant such as HFA134a or HFA227 together with optional solvent such as ethanol. The reservoir 2 is filled through an inlet closed by a plug 4.

A valve 9 is provided having an inlet 11 communicating with the volume 3 of the reservoir 2. As shown in FIG. 1, the inlet 11 may comprise a hollow tube 13 spanning between volume 3 of the reservoir 2 and an interior of a valve body 10 of the valve 9. The valve 9 further comprises a valve stem 12 which is axially moveable within the valve body 10 from a non-dispensing, closed position as shown in FIG. 1 to a dispensing, open position shown in FIG. 2. The valve stem 12 comprises a first flange 17 located within the interior of valve body 10. A spring 21 extends between an internal shoulder of the flange 17 and a shoulder of the valve body 10 to bias the valve stem 12 into the non-dispensing position of FIG. 1. The valve stem further comprises second and third flanges 18 and 19 located exterior to the valve body 10, the use of which will be described below.

A distal end of the valve stem 12 which protrudes from the interior of the valve body 10 comprises a hollow duct 22 terminating in an outlet 14. A radial transfer port 20 is formed in the valve stem 12 providing communication between an exterior of the valve stem 12 and the hollow duct 22. A spray pattern block 15 may be located on the distal end of the valve stem 12 as shown in FIG. 1 to improve atomisation of product dispensed through the valve 9. The spray pattern block 15 may be provided with turbulence generating formations 23 in order to maximise turbulence of the dispensed product.

An outer end of the valve body 10 is closed and sealed by means of an elastomeric seal 16. The valve stem 12 forms a sliding interference fit with an aperture formed at the centre of the outer seal 16.

As shown in FIG. 1, the valve 9 is located in a distal end 24 of a pole piece 5 formed from a piece of magnetisable material such as a ferrous material such as mild steel or iron. The pole piece 5 is elongated and contacts at an upper end a pair of bars 6 again formed from a ferrous material such as iron or steel. An enlongate resiliently flexible armature 8 made from a magnetisable material such as spring steel is sandwiched between the bars 6 and extends therefrom downwardly into close proximity with the distal end 24 of the pole piece 5 and the valve 9. As shown in FIG. 1, a distal end of the armature 8 is provided with an aperture through which the valve stem 12 extends. As shown in FIG. 1, the armature 8 is coupled to the valve stem 12 at a position between the second and third flanges 18, 19 such that sideways movement of the distal end of the armature 8 (as viewed in FIG. 1) in either direction causes the valve stem 12 to move with the armature 8.

The dispensing apparatus further comprises an electromagnet 7 in the form of a coil of electrically conductive wire which may be energised by an electric current using contacts and a power supply which are not shown in the schematic figures. An alternative means of providing the electric current, (other than a battery), may be utilised, such as current induced by the movement of the inhaler or its components.

In the non-dispensing position of FIG. 1, the transfer port 20 of the valve stem 12 lies outside the valve body 10 sealed by the outer seal 16 such that there is no path to atmosphere for pressurised product contained in the reservoir volume 3. In order to dispense a dose of pressurised product from the reservoir 2, the electro-magnetic coil 7 is energised causing a magnetic field to be induced in the armature 8. Consequently, the distal end of the armature 8 is caused to be attracted to the distal end 24 of the pole piece 5. This movement of the armature 8 causes the valve stem 12 to be moved inwardly relative to the valve 9 into the position shown in FIG. 2 wherein the transfer port 20 of the valve stem 12 is moved into the interior of the chamber body 10 past the outer seal 16. In this position, flow of pressurised product from the volume 3 of the reservoir 2 may take place via the inlet tube 11, the interior of the valve body 10, the transfer port 20 and the hollow duct 22 of the valve stem. The product exits the outlet 14 of the valve stem 12 and then passes through the pattern spray block 15 and is then dispensed to atmosphere. As will be clear, dispensation in this way continues until the valve stem 12 is moved back into position shown in FIG. 1. In the first embodiment shown in FIG. 1, de-energisation of the electromagnet 7 causes a cessation of the magnetic field induced in the armature 8. At this point, the natural resilience of the armature 8 leads to the armature 8 tending to straighten thus moving the armature 8 out of contact with the distal end 24 of the pole piece 5 and movement of the valve stem 12 back into the non-dispensing position shown in FIG. 1. This movement may optionally be aided by provision of the internal spring 21 in the valve 9, although it will be appreciated that the spring 21 may be dispensed with and the armature 8 alone used to move the valve stem 12 back into the non-dispensing position. The armature 8 is prevented from fully straightening by contact of the first flange 17 of the valve stem 12 with the outer seal 16 of the valve 9. By timing the period for which the electromagnet 7 is energised, and the orifice size of the transfer port 20 and other orifices of the flow path, the volume of product dispensed in a single dose may be accurately controlled. Preferably the volume of each dose of product is between 10 and 300 microlitres. More preferably the volume is between 25 and 100 microlitres.

Accurate timing of the energisation of the electro-magnet 7 is controlled by a microprocessor and control software (not shown in the schematic figures) housed in the metered dose inhaler. The initialisation of a dispensing cycle may be commenced by operation of a manual trigger by the user or by using some other triggering event such as inhalation of the user.

The pressure of the product in the reservoir 2 is preferably between 15 and 200 psig and more preferably the pressure is approximately 60 psig at a room temperature of approximately 20 degrees Celsius.

The piece of magnetisable material to which the armature 8 is attracted need not be elongated and in this embodiment need not extend into contact with the bars 6. Instead a discrete piece or block of magnetisable material may be provided in close proximity to the valve 9. The piece of magnetisable material may form part of the valve 9.

Figure 3:
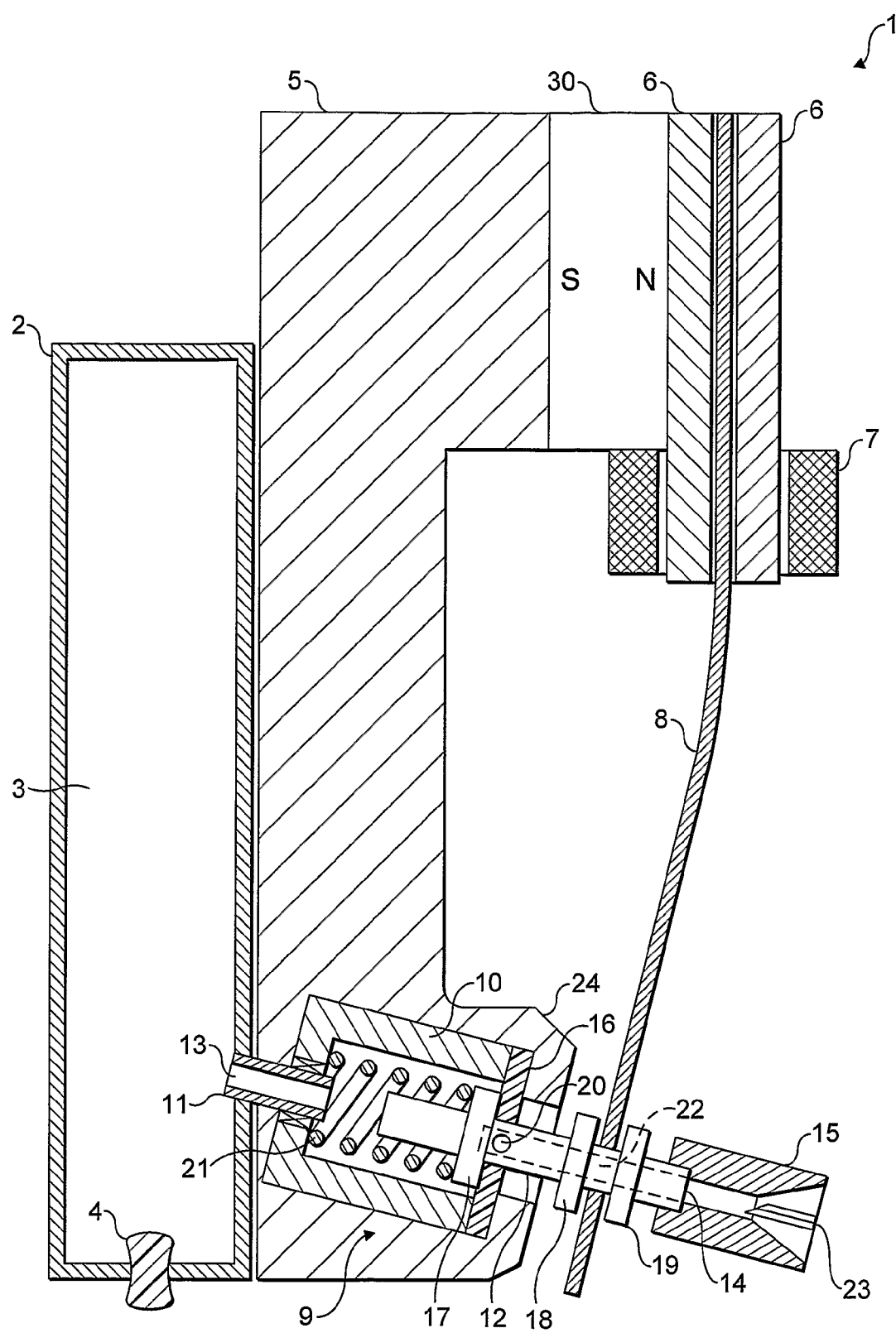
FIG. 3 is a schematic cross-sectional view of a second embodiment of dispensing apparatus in accordance with the present invention in a non-dispensing position.

FIG. 3 shows a second embodiment of dispensing apparatus according to the present invention. Like reference numerals have been used to reference like components with the first embodiment. Compared to the first embodiment, the apparatus has been amended by the provision of a permanent magnet 30 between the pole piece 5 and the bar 6. In other respects the construction of the apparatus is the same. In this embodiment when the electromagnet 7 is energised, the armature 8 is attracted into contact with the distal end 24 of the pole piece 5 as in the first embodiment. However, contact between the armature 8 and the pole piece 5 closes a permanent magnetic circuit incorporating the pole piece 5 and the permanent magnet 30, bar 6 and armature 8. Thus, in this embodiment when the electromagnet 7 is de-energised, the armature 8 remains in contact with the distal end 24 of the pole piece 5 since the attractive force between the armature 8 and the pole piece 5 caused by the permanent magnet 30 is greater than the force created by the resilience of the armature 8. Contact remains and hence dispensing of pressurised product continues until the electromagnet 7 is re-energised with an opposing polarity causing the armature 8 to be induced with a magnetic field of opposed polarity which leads to disruption of the attractive force between the distal end 24 of the pole piece 5 and the armature 8. Consequently, the armature 8 breaks contact with the pole piece 5 and moves back into the non-dispensing position shown in FIG. 3.

Thus, in this embodiment, two energisations of the electromagnet 7 are required to carry out the dispensation of a single metered dose. The first energisation moves the valve stem 12 into the dispensing position to commence dispensation and the second energisation overcomes the attractive force between the armature and the permanent magnetic circuit to move the armature 8 back into the non-dispensing position to stop dispensation. By correct timing of the first and second energisations of the electromagnet 7, the volume of the metered dose dispensed may be accurately controlled.

The direction of valve operation of the first and second embodiments may be reversed such that attraction of the armature 8 into contact with the pole piece 5 moves the valve stem 12 into a non-dispensing position and movement of the armature 8 out of contact with the pole piece 5 moves the valve stem 12 into a dispensing position.

For both the first and the second embodiments, the apparatus may be amended by the provision of a complimentary piece of magnetisable material forming a second pole piece (and optionally a second permanent magnet) arranged to have a distal end opposing the distal end 24 of the first pole piece 5 such that the armature 8 and valve stem 22 lie in an air gap between the end faces of the pole pieces. With such an arrangement, by choosing the direction of the current flow in the electromagnet 7, the armature 8 can be caused to be attracted to one or other of the pole pieces. Attraction to one pole piece can be used to move the valve stem 12 into the dispensing position and attraction towards the other pole piece can be used to move the valve stem 12 into the non-dispensing position. This arrangement allows for opening and closing of the valve 9 both to be achieved using magnetic attractive forces which allows for a potentially higher speed of response and more certain closing of the valve. In turn this can increase the accuracy of the metered dose dispensed.

The invention claimed is:

1. A pressurised metered dose inhaler comprising: a reservoir for containing pressurised product, a valve having an inlet communicating with the reservoir and an outlet through which product is dispensed in use, a piece of magnetisable material, an armature extending into proximity with the valve, and an electromagnet surrounding at least a portion of the armature, wherein the armature is coupled to, or forms part of, the valve such that controlled energisation of the electromagnet causes the armature to be either attracted to or repelled from the piece of magnetisable material one or more times to operate the valve for a controlled time period to effect dispensation of a metered dose of pressurised product from the reservoir through the valve outlet of the pressurised metered dose inhaler, wherein the valve comprises a valve stem axially movable within a valve body between open and closed positions, wherein with the valve stem in the open position dispensation of product through the valve outlet is enabled, wherein the armature is coupled to, or forms part of, the valve stem, wherein the valve stem comprises one or more flanges and wherein the armature engages the valve stem by contact with the one or more flanges.

2. A pressurised metered dose inhaler as claimed in claim 1 wherein the piece of magnetisable material is in proximity to the valve.

3. A pressurised metered dose inhaler as claimed in claim 1 wherein attraction of the armature to the piece of magnetisable material opens the valve to effect dispensation of a metered dose of product from the reservoir through the valve outlet.

4. A pressurised metered dose inhaler as claimed in claim 1 wherein repulsion of the armature from the piece of magnetisable material opens the valve to effect dispensation of a metered dose of product from the reservoir through the valve outlet.

5. A pressurised metered dose inhaler as claimed in claim 1 wherein the armature is resilient and, in the absence of magnetic forces, acts on the valve stem to bias the valve stem into a closed position.

6. A pressurised metered dose inhaler as claimed in claim 1 wherein the valve comprises an internal spring bias biasing the valve stem into the closed position.

7. A pressurised metered dose inhaler as claimed in claim 1 wherein the valve stem comprises a transfer port communicating with the valve outlet and wherein the valve comprises an outer seal sealing the transfer port from the valve inlet when the valve stem is in the closed position.

8. A pressurised metered dose inhaler as claimed in claim 7 wherein movement of the valve stem into the open position moves the transfer port past the outer seal into communication with the valve inlet to enable product dispensation through the valve via the transfer port and valve outlet.

9. A pressurised metered dose inhaler as claimed in claim 8 wherein the outer seal is formed from an elastomeric material.

10. A pressurised metered dose inhaler as claimed in claim 1 further comprising a permanent magnetic circuit comprising one or more permanent magnets.

11. A pressurised metered dose inhaler as claimed in claim 10 wherein the piece of magnetisable material forms a single pole piece extending from the one or more permanent magnets into close proximity with the valve.

12. A pressurised metered dose inhaler as claimed in claim 11 wherein movement of the armature into contact with the pole piece on energisation of the electromagnet with a first polarity completes the permanent magnetic circuit.

13. A pressurised metered dose inhaler as claimed in claim 12 wherein the attractive permanent magnetic force between the pole piece and the armature when the pole piece and armature are in contact exceeds the resilience of the armature such that when the electromagnet is de-energised the pole piece and armature remain in contact.

14. A pressurised metered dose inhaler as claimed in claim 13 wherein energisation of the electromagnet with a second, opposed, polarity causes the pole piece to repulse the armature such that the armature breaks contact with the pole piece.

15. A pressurised metered dose inhaler as claimed in claim 10 comprising two pieces of magnetisable material forming two pole pieces extending from the one or more permanent magnets into close proximity with the valve to define an air gap in which the armature extends.

16. A pressurised metered dose inhaler as claimed in claim 15 wherein energisation of the electromagnet with a first polarity moves the armature into contact with a first of the two pole pieces to complete the permanent magnetic circuit.

17. A pressurised metered dose inhaler as claimed in claim 16 wherein the attractive permanent magnetic force between the first pole piece and the armature when the first pole piece and armature are in contact exceeds the resilience of the armature such that when the electromagnet is deenergised the first pole piece and armature remain in contact.

18. A pressurised metered dose inhaler as claimed in claim 17 wherein energisation of the electromagnet with a second, opposed, polarity causes the armature to be attracted to a second of the two pole pieces such that the armature breaks contact with the first pole piece.

19. A pressurised metered dose inhaler as claimed in claim 1 wherein the controlled time period of operation of the valve is between 25 and 250 ms.

20. A pressurised metered dose inhaler as claimed in claim 1 wherein the metered dose has a volume of between 5 and 300 microlitres.

21. A pressurised metered dose inhaler as claimed in claim 20 wherein the metered dose has a volume of between 10 and 100 microlitres.

22. A pressurised metered dose inhaler as claimed in claim 1 further comprising a pressurised product contained in the reservoir.

23. A pressurised metered dose inhaler as claimed in claim 22 wherein the pressurised product is maintained at a pressure of between 15 and 200 psig.

24. A pressurised metered dose inhaler as claimed in claim 23 wherein the pressurised product is maintained at a pressure of approximately 60 psig at a room temperature of approximately 20 degrees Celsius.

25. A pressurised metered dose inhaler comprising: a reservoir for containing pressurised product, a valve having an inlet communicating with the reservoir and an outlet through which product is dispensed in use, a piece of magnetisable material, an armature extending into proximity with the valve, and an electromagnet surrounding at least a portion of the armature, wherein the armature is coupled to, or forms part of, the valve such that controlled energisation of the electromagnet causes the armature to be either attracted to or repelled from the piece of magnetisable material one or more times to operate the valve for a controlled time period to effect dispensation of a metered dose of pressurised product from the reservoir through the valve outlet, and said pressurised metered dose inhaler further comprising a pressurized product contained in the reservoir, and wherein the pressurised product comprises a volatile propellant, wherein the valve comprises a valve stem axially movable within a valve body between open and closed positions, wherein the valve stem comprises one or more flanges and wherein the armature engages the valve stem by contact with the one or more flanges.

26. A pressurised metered dose inhaler as claimed in claim 25 wherein the propellant comprises one or more of HFA134a, HFA227, with or without ethanol being present at a level of between 1 and 30%.

27. A pressurised metered dose inhaler as claimed in claim 22 wherein the pressurised product contains a pharmacologically active formulation.

28. A pressurised metered dose inhaler as claimed in claim 1 further comprising electronic means for locking out operation of the valve for a predetermined time period after each actuation of the valve.

29. A method of dispensing a pressurised product from a metered dose inhaler of the type comprising a valve having an inlet communicating with a reservoir in which the pressurised product is contained and an outlet, comprising the steps of: coupling an armature of an electromagnet to, or forming an armature of an electromagnet as part of, a valve stem of the valve, wherein the valve stem comprises one or more flanges and wherein the armature engages the valve stem by contact with the one or more flanges, moving the armature of the electromagnet by controlled energisation of the electromagnet towards or away from a piece of magnetisable material one or more times so as to move the valve stem from a non-dispensing position to a dispensing position for a controlled time period to effect dispensation of a metered dose of pressurised product through the valve outlet of the pressurised metered dose inhaler.

30. A method as claimed in claim 29 wherein energisation of the electromagnet moves the valve into the dispensing position.

31. A method as claimed in claim 30 wherein on deenergisation of the electromagnet the armature is moved away from the piece of magnetisable material by resilience of the armature so as to move the valve into the non-dispensing position.

32. A method as claimed in claim 30 wherein the metered dose inhaler further comprises at least one permanent magnet arranged such that on de-energisation of the electromagnet the armature remains in contact with the piece of magnetisable material until the electromagnet is reenergised with a current of opposing polarity.

33. A method as claimed in claim 29 wherein the controlled time period is between 25 and 250 ms.

34. A method as claimed in claim 29 wherein the volume of the metered dose is between 5 and 300 microlitres.

35. A pressurized metered dose inhaler as claimed in claim 1 wherein the valve stem has a fluid conduit formed therein and through which pressurized product passes during dispensing.

36. A pressurised metered dose inhaler as claimed in claim 25 wherein the pressurised product contains a pharmacologically active formulation.

* * * * *